(12) United States Patent
Vurens et al.

(10) Patent No.: US 6,678,043 B1
(45) Date of Patent: Jan. 13, 2004

(54) METHODS AND APPARATUS FOR SURFACE ANALYSIS

(76) Inventors: Gerard H. Vurens, 188 Walter Hayes Dr., Palo Alto, CA (US) 94303; David L. Klein, 1975 Alma St., Palo Alto, CA (US) 94301

( * ) Notice: Subject to any disclaimer, the term of this patent is extended or adjusted under 35 U.S.C. 154(b) by 344 days.

(21) Appl. No.: 09/703,411

(22) Filed: Oct. 31, 2000

(51) Int. Cl.[7] ................................................ G01N 21/88
(52) U.S. Cl. ..................... 356/237.2; 356/369; 382/145
(58) Field of Search ..................... 356/369, 237.2, 356/237.3, 237.4, 237.5, 237.1; 348/87, 129, 130; 382/145, 147

(56) References Cited

U.S. PATENT DOCUMENTS

| | | | |
|---|---|---|---|
| 5,121,438 A | * 6/1992 | Kawauchi et al. | 382/141 |
| 5,432,545 A | 7/1995 | Connolly | |
| 5,509,084 A | 4/1996 | Tanaka | |
| 5,517,234 A | * 5/1996 | Gerber et al. | 348/126 |
| 5,726,455 A | 3/1998 | Vurens | |
| 5,809,165 A | * 9/1998 | Massen | 382/168 |
| 5,818,443 A | * 10/1998 | Schott | 382/141 |
| 6,031,615 A | 2/2000 | Meeks | |
| 6,130,749 A | 10/2000 | Meeks | |
| 6,134,011 A | 10/2000 | Klein | |
| 6,198,533 B1 | 3/2001 | Meeks | |
| 6,229,610 B1 | 5/2001 | Meeks | |
| 6,268,919 B1 | 7/2001 | Meeks | |
| 6,392,749 B1 | 5/2002 | Meeks | |

OTHER PUBLICATIONS

Vurens & Klein, SPIE vol 3619, 1999, P 27.
Klein & Vurens, SPIE vol 3619, 1999, p. 18.
Meeks et al. J. Tribology 117, 1995 p. 112.
Bright & Marineniko, Microscopy: The Key Research Tool 22(1):21–28 (Mar. 1992, Electron Microscopy Society of America, special publication).

* cited by examiner

Primary Examiner—Richard A. Rosenberger
(74) Attorney, Agent, or Firm—Stanley Z Cole; Edward Berkowitz

(57) ABSTRACT

There is described method and apparatus to create multi-dimensional non-spatial histograms of surfaces and to compare such histograms to show whether the surfaces substantially conform to one another. This analysis is particularly applicable to comparing die on wafers to determine whether manufactured devices conform to a master or whether one die is like another.

15 Claims, 3 Drawing Sheets

METHODS AND APPARATUS FOR SURFACE ANALYSIS

FIELD OF THE INVENTION

This invention relates to surface measurement, particularly of patterned surfaces to analyze surface characteristics of a patterned workpiece under study.

BACKGROUND OF THE INVENTION

In processes employed today in the manufacture of solid state devices from wafers, complex processes are followed which frequently leave the wafer with certain surface (and subsurface) features, residues and characteristics. For example, in making integrated circuits and chips from semiconductor wafers and for micro-mechanical apparatus, a large number of manufacturing steps are employed to produce structural features such as bridges, cavities, interconnects, vias, etc. and may include, for example, spin-on photoresists, photoresist processing, etching, deposition of films (both dielectric and conducting), ion implantation, chemical mechanical polishing (CMP) and other polishing steps, which may, with other processes, all be included in the treatment of and creation of an ultimate device. Similarly, processes are employed in manufacture of magnetic hard disks and magnetic read/write heads. Aluminum oxide/titanium carbide (AlTiC) wafers, used in the thin film magnetic head industry and other semiconductor materials such as gallium arsenide, used for specialized devices, are processed in a similar manner which can be expected to leave surface and sub-surface effects which can significantly effect the ultimate product. For the purposes of this description, "surface" includes not only the outer extreme of a layer or substrate but also the optically accessible interface between adjacent layers.

It is known in prior art to acquire spatial images of surface features of wafers containing numerous device units ("die"), to evaluate these for consistency of structure and to discover deficient die, and similarly to compare nominally identical wafers and components thereon. A variety of apparatus is known for this purpose, with a unifying characteristic that an image of the surface under inspection is acquired. This image is a true mapping of a spatial image of a tangible two dimensional (albeit, microscopic) surface of interest. In manufacture of semiconductor die and like articles, a large number of identical structures are formed on a common substrate, or wafer and the efficacy of the processing steps becomes evident in the percentage ("yield") of acceptable device units or equivalent articles which are finally realized on conclusion of the processing steps. Individual die, and the wafer as a whole present a discretely patterned surface. Defects which appear at intermediate stages of the processing are determinative of the upper limit to yield and thus there is an advantage in evaluating die at various stages of manufacture. In evaluating the physical character of the surfaces for comparison with like surfaces or for comparison with some reference surface, the prior art requires image processing to locate the corresponding spatial features by pattern recognition procedures, a slow, cumbersome (and error prone) process in the context of the duration of process steps. Yet, this is the type of processing in use today.

As technology develops in the semiconductor manufacturing fields, the manufacturers are forced to tighter process tolerances and are compelled to use process controls capable of analyzing key factors to assure satisfactory results and to control and increase yields and device performance. This is a result of defects becoming smaller in size as well as new defect sources from material changes and process variations require more responsive instrumentation and techniques to inspect and analyze manufactured products for anomalies and defects.

Instrumentation exists that can illuminate the surface with controlled optical polarization states and inspect and analyze for film thickness and defects. Many such instruments have more than one concurrent data channel, e.g., sensitivity to scattered light, polarization specific reflectance, phase differences at selected angles of incidence, selectable narrowly wavelength dependance and phase difference information from specularly reflected light derived from a stabilized source. These channels may typically have a known relationship for their collected data as a function of the sample's properties such as, the shape, composition and/or thickness of each layer of a stack of films or the composition and size of particles at the interface.

Polarization tools such as a surface reflectance analyzer (SRA) measure a combination of scattering, reflectance, polarization ratio, and phase differences. These measurements can be made as a function of the angle of incidence, wavelength, and type of incident polarization. Any combination of these measurements can be used for multidimensional histogram analysis. In this invention, suface reflectance and optical reflectance analysis are terms intended as generic representation of these test processes and devices as well as equivalent techniques and instruments.

An example of such prior instrumentation is contained in U.S. Pat. No. 6,134,011, commonly assigned, and incorporated for reference herein. Such instrumentation is available from HDI Instrumentation located in Santa Clara, Calif. A preferred such unit is identified as an SRA Instrument. The deviations that were addressed in prior art applications included variations in uniformity or constant thickness, etc. for a workpiece of a nominally homogeneous external surface. The processes that have existed, principally address relatively slowly varying observables. Prior instrumentation however, has not heretofore been addressed to the problem of enabling surface determinations as to investigate or evaluate or compare discrete, systematic variations on surfaces comprising patterns on samples or to the concern that can arise in the semiconductor manufacturing field of determining where defects exist.

SUMMARY OF THE INVENTION

This invention is concerned with rapid, concurrent measurement techniques where the observeable data changes rapidly in respect to spatial variables, which is typical for patterned surfaces. The invention describes a way to analyze the data streams from several related data channels directed toward comparative examination of patterned surfaces using a multi-dimensional histogram. In its simplest form, data from two channels are combined in a two dimensional (2D) histogram. Multi-dimensional histogram analysis has, been used to correlate medical images (see U.S. Pat. No. 5,509,084), to perform color separation (see U.S. Pat. No. 5,432,545), or in measuring thin film properties in magnetic recording disks (see Vurens and Klein SPIE Vol 3619, 1999, page 27; Klein and Vurens, SPIE Vol 3619, 1999, page 18; Meeks et al. J. Tribology 117; 1995, page 112). In general higher dimensional histograms can also be used (e.g., 3D or 4D), or multiple correlated 2D histograms may be used for data analysis. The prior art may be generally characterized as employing multidimensional histograms for the purpose of examining non-uniformities of slowly varying characteristics in a single workpiece under investigation.

A multi-dimensional histogram analysis has unique advantages in dealing with data obtained from scanning patterned surface workpieces such as device bearing substrates, for which semiconductor wafers serve as an example. For the purposes of this work, "pattern" is meant to convey systematically ordered features, spatial and/or compositional, which exhibit substantial discontinuities or posses relatively large spatial derivatives. As described these wafers typically have complex patterns of multiple and overlapping films on their surfaces forming a microscopic three dimensional spatial topology e.g., die, which is repeated over the wafer area. Typically, one is interested in the properties of certain regions that contain a unique film pattern on the sample. Currently, in order to study these particular regions, software is used that automatically compares different (nominally identical) areas using programs developed for pattern recognition of spatially imaged regions. Sometimes this approach is used to compare a region of interest with a comparable region nearby on the surface of the same, or disposed on a nominally identical wafer. This is sometimes referred to as die-to-die comparison. The comparison may be directed from a die under examination to another reference, such as a specified model or master or simulation. This type of software for recognition and comparison of spatial images is complex, slow and prone to error. For certain applications the proposed histogram analysis of the present invention can be used to analyze uniformity across patterned surfaces quickly and accurately without the use of such spatial imaging, spatial image recognition and procedures to make spatial image comparisons. For comparison of workpieces, whether patterned or nominally uniform, the differences in non-spatial multi-dimensional histograms provides rapid and reliable detection and determination of the aberrant workpiece or segment thereof.

The purposes of this invention are achieved by collecting various data streams from an instrument optically scanning a patterned surface being examined. This can be done by simultaneously detecting correlated optical data streams representing, for example, reflectance and phase difference of controlled and resolved polarization states. The acquired data streams may be stored in the form of sequential correlated records or processed for storage and use as multi-dimensional histograms. In the latter case, the sequential records may be sorted to form multi-dimensional histograms of desired characteristics. Importantly, in the preferred usage, the histogram retains a direct relationship to the original data sets. This data is non-spatial in character; consequently, two such histograms of nominally identical structures may be directly compared on a cell by cell basis in the non-spatial domain thus avoiding reliance upon pattern recognition and pattern alignment. This permits use of the histogram technique to distinguish areas with large differences as well as to permit highlighting areas for smaller variations and enables locating differences for nominally corresponding patterns.

BRIEF DESCRIPTION OF THE DRAWINGS

For a better understanding of the present invention, reference is made to the accompanying drawings, which are incorporated herein by reference, and in which.

DETAILED DESCRIPTION OF THE INVENTION

Figure 1:
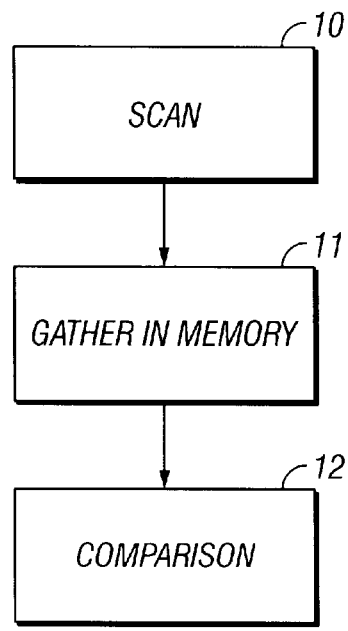
FIG. 1 is a schematic overview of a system forming the context for the invention.
Figure 2:
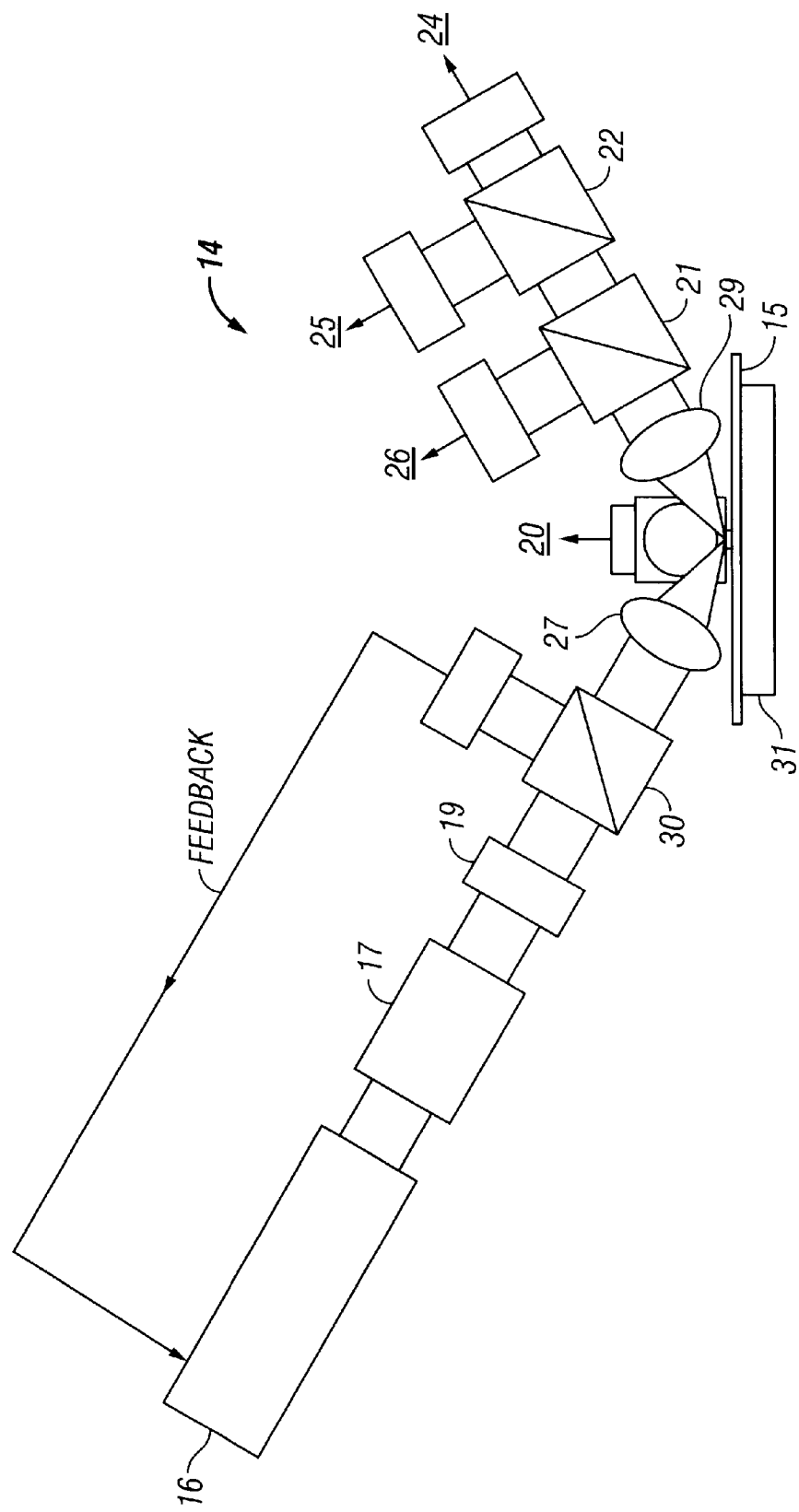
FIG. 2 describes a surface reflectance tool suitable for use in the invention.

FIG. 1 shows the elements of the invention in block diagram form. At block 10, a workpiece, in this instance a first workpeice, is scanned by a surface reflectance analyzer. This equipment is more fully discussed in connection with FIG. 2 hereafter. The analyzer generally produces more than one optical reflectance parameter from a single spatial point of the workpiece under examination as will be explained more fully in connection with FIG. 2. A typical such system measures simultaneously several parameters, such as S polar and P polar reflected intensities and the phase difference therebetween, and the scattered light associated with the point under examination. The outputs from the reflectance analyzer in FIG. 2 are directed to block 11 where the output data is gathered and sorted to create selected multi-dimensional histograms representing the optical reflectance response of the workpiece.

In general, a complete surface reflectance analysis scan can provide a number, such as three, unique and independent specular reflectivity data outputs. In this disclosure and particularly in FIG. 2, we focus upon measuring P polar reflectivity, S polar reflectivity, and phase shift. Equivalent information can also be obtained with a different set of measurements. For example, a standard ellipsometer measures a set of parameters that are called psi, del, and reflectivity. These three parameters can be mathematically transformed to yield the P polar reflectivity, S polar reflectivity, and phase shift data mentioned above. As an example, current commercial surface reflectance analyzer systems (HDI units, for example) measure three parameters that are called "P polar reflectivity", "phase contrast", and "enhanced phase contrast". The terms "phase contrast" and "enhanced phase contrast" are the names of two detectors of a known commercially available surface reflectance analyzer. Each of these channels provide a unique signal that is related, but not identical, to the phase shift of the reflected light. When these two data signals are mathematically combined with the P polar data, they can be used to calculate the phase shift of the reflected light. The description of the design and use of these phase shift sensitive detectors is given in U.S. Pat. No. 6,134,011, which is incorporated herein by this reference for a more complete disclosure of such detectors.

The parameters: P polar reflectivity; phase contrast; and enhanced phase contrast are equivalent to the ellipsometry data as well as the P polar reflectivity, S polar reflectivity, and phase shift data discussed above. These parameters are readily measured using a setup similar to that depicted in FIG. 2. The choice of parameters, and parameters to be measured is based upon theoretical and experimental optimization of the signal to noise for the type of substrate, surface and/or film of interest for measurement.

The multidimensional histogram(s), typically in accordance with this invention, is held in memory for use in a comparison to data derived from another workpiece or from a reference. Thus, a second workpiece may be examined by the surface reflectance analyzer in similar fashion and that output will be similarly processed. A comparison of the respective multi-dimensional histograms from the first and second workpiece is made in block 12. Alternatively, the comparison may be directed to a simulation of the expected reflectance analysis derived from a model. A discussion of blocks 11 and 12 and particularly their composition and performance also appears hereafter.

Referring now to FIG. 2, there is shown a schematic of a surface reflectance analyzer. Light is emitted from a stabilized diode laser 16. A linear polarizer 17 and quarter wave plate 19 are used to make this light circularly polarized. A reference beam is generated and then the primary beam is focused onto a sample 15. Light scattered from the workpiece is collected by integrating sphere 20. The reflected light is recollimated and passes through a set of prisms 21 and 22 that separate out the P Polar 24 and S Polar 25 refectivity signals as well as a signal that is sensitive to the relative phase shift of the S and P polar light, identified as the phase contrast 26. Lenses 27 and 29 focus the incoming and the outgoing light beams. With a system as described one can simultaneously measure the four optical parameters, P polar reflectivity 24, S polar reflectivity 25, phase contrast 26 and scattered light intensity measured at the output of the integrating sphere 20. Typically these signals are measured at speeds up to 10 MHz as a workpiece or sample 15 is translated and/or rotated beneath the optics. It is also practice in this art in collecting data and modifying data into histograms, to use less than all 4 outputs notwithstanding that the tool in use may be capable of such results.

Further about the design of the surface reflectance analyzer, a commonly used angle of incidence (in respect to the normal to the substrate) for the measurement is approximately 60 degrees. This corresponds to values for Brewster's angle for a typical media interface, and typically is used when the reflectance analyzer 14 is used for measurements of certain selected layers on a substrate. Since reflectance analyzers used for such a purpose exist, and work well for the purposes of this invention, such a design is being described to make the required measurements and create the data required by this invention. As is known in the art, the system described requires narrow wavelength light that is highly stable in intensity and wavelength. In this connection a beam splitter 30 permits a reference beam to be used to enhance the stability of laser 16 over time. A stabilized laser of the type useful in the analyzer is described more fully in U.S. Pat. No. 5,726,455. Feedback may also be used to assure the stability of the light source used in the analyzer as illustrated in FIG. 2.

The system of FIG. 2 provides a very stable source of circularly polarized light of narrow bandwidth for incidence at a precisely selected angle to the normal, followed by detection of the S polar and P polar components of reflected light and their phase difference. Relative displacement of a workpiece in the plane defined by the normal provides for the physical scanning of the workpiece in a systematic manner. The several optical reflectance channels of the instrument of FIG. 2 are related by Fresnel's equations, as discussed in connection with FIG. 4 below. For the purposes of the present work, the incident (circularly polarized) radiation, yields a specularly reflected component containing both S polar and P polar components with an observable phase difference therebetween, a scattered component and an absorbed component. The reflectance analyzer for purposes of this invention should include a highly stable movable table or stage 31 supporting and moving the workpiece relative to the reflectance analyzer to permit data gathering from point to point along the entire surface of the workpiece 15. The workpiece may be rotated at a uniform rate to facilitate the gathering of the data.

Figure 3:
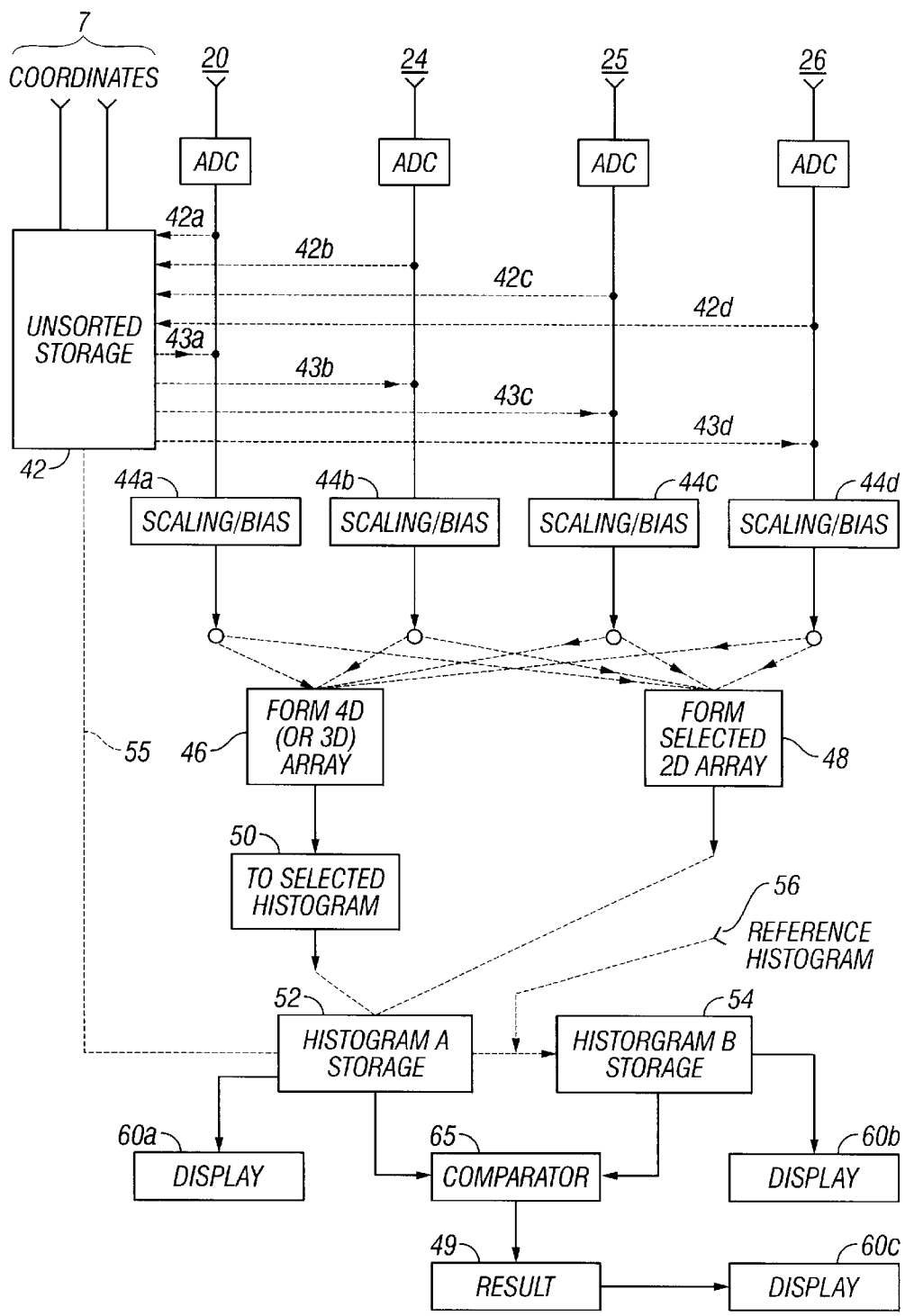
FIG. 3 illustrates operations on data derived with the module of FIG. 2 for practice of the invention.

The reflectivity parameters obtained with the optical reflectance module of FIG. 2 (or similar apparatus), scattered light intensity, P and S polar reflectivity and phase difference therebetween are next directed to a data processing system as described in connection with FIG. 3. The respective signals 24, 25, 26, and 20 are digitized by corresponding analog-to-digital converters (ADCs) and may optionally be directed via paths $42_{a-d}$ to mass storage 42 to retain the full precision of the serially acquired (unsorted) data. Subsequent processing of this data is facilitated on paths $43_{a-d}$ for selected processing.

Because each parameter is capable of digital conversion to relatively high precision, the memory requirement for storage of the sorted array (histogram) may exceed the available memory storage capacity when the full precision of the acquired parameter value specifies a portion of the memory cell address. The digital precision of each parameter value is therefore selected by shift operations and biased in conventional fashion at blocks $44_{a-d}$.

In the general case, sorting of the data may take the form of a 4 dimensional array, any of four combinations of 3 of the parameters to yield one or more 3D arrays, or any pair of parameters to form one (or more) 2D array(s). Each datum is treated as a displacement along the corresponding parameter axis, forming a partial address to locate that array element. For a 2D histogram, the two partial addresses constitute together the full address of a memory cell, which cell is then incremented. In this manner the data stream is sorted to form the desired 2D (or higher dimensioned) histogram.

It is completely equivalent to form the 2D histogram directly, as by sort operation 48, or alternatively, to operate on a higher dimensioned histogram as at block 50 from block 46, to result in the identical 2D histogram. Constraints may be imposed on the serial data stream to directly produce the equivalent 2D slice or projection, if desired. The choice of what parameters to sort, or ignore, depend upon the nature of the workpiece, and the choice of the manner of sorting depend upon the complexity of the pattern characterizing the workpiece, the available memory and time constraints.

It is usually desired to compare similar histograms. (The term "histogram" in this invention description is meant to mean a multidimensional histogram). For this purpose, one or another or both histograms for comparison are retained in storage areas 52 and/or 54. One of the histograms is, by convention, the reference histogram 56 and this set of sorted data may be a controlled representation of a standard workpiece, or the histogram resulting from simulation or other model calculation.

In the comparator block 65, the biased/scaled histograms are compared cell by cell as differences (or ratios) to yield the net histogram in block 49 which then may be displayed at display 60c. Histograms A and B may be viewed at displays 60a and 60b respectively.

Formation of a multidimensional histogram proceeds by treating each parameter of the datum (whether at original precision or rounded downward) as an address: and incrementing the location so specified in the multidimensional space. For convenience in most operations, it is desirable to work with a 2D histogram. Where the data are acquired as a 3D correlation, one of the; three parameters may be (a) ignored or (b) required to exhibit a value within a selected range. The case (a) represents integration over the ignored parameter and the case (b) is simply a slice from a virtual 3D histogram.

For the present invention, the details of the physical surface (or portion thereof) are represented in the histogram, but not as a spatial image. That is, the optical response of the surface at different Cartesian coordinates might contribute to the same cell of the histogram. The histogram represents a unique transformation into the particular optical parameter space of the spatial pattern characterizing the structure under examination. The transformation is not generally isomorphic, but for purpose of comparison with a reference histogram this is not relevant. As the optical point of incidence moves in relation to the physical surface (via mechanical stage, rotation of the workpiece, etc), the patterned character of the surface introduces a varying angle of optical incidence in respect to portions of the patterned workpiece, thereby affecting the response of the several data channels.

Figure 4:
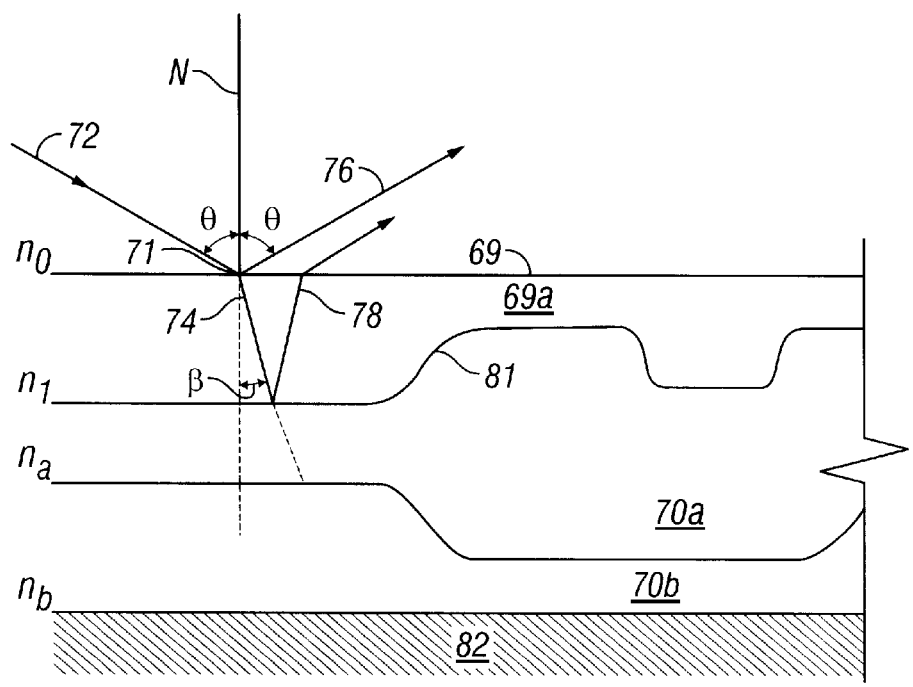
FIG. 4 shows the various related optical components in the context of the inventive procedure.

FIG. 4 depicts a typical multi-layered workpiece. In common practice, a passivating layer 69 is formed over a (representative) structure of (dielectric) layers 70a and 70b having corresponding indices of refraction $n_a$ and $n_b$, and subject to circular polarized, incident radiation 72 propagating in medium of index $n_0$ and intercepting the interface formed by the external surface of layer 69a (refractive index=n) at angle θ at a point 71. The angle θ is taken in relation to the normal to the substrate 82. A portion 76 of that incident radiation 72 is reflected at angle θ which contains a first portion polarized in the plane of incidence ("P polar") and a second portion polarized orthogonal to the plane of incidence ("S polar). A refracted component 74 propagates through medium 69a at an angle β characteristic of the interface of media 69a and 70a and interacts at the interface of layer 70a and 69a with reflectance and transmission. Reflection and refraction similarly occur at successive interfaces and expected attenuation. Scattered light originates in interactions of photons with scattering centers of dimensions approaching the wavelength of the radiation.

Close to the polarizing angle, the reflected P polar component undergoes a phase shift of π and the refracted component accrues phase shift in traversing the medium. The reflected S polar component is invariant in phase. These relationships may be squared to yield the several relative intensities stated as reflectivities. An important observation for the purpose of the present invention is that relative translation of the workpiece along the x axis presents a different point 81 for interception of the refracted light 74.

It should be emphasized that the evaluation or comparison of workpieces, whether die or other constructions, may occur at intermediate steps of fabrication. Reference herein to a "surface" is not to be limited to the external surface of a fully formed device unit or die, but rather is inclusive of any interface accessible to the reflectance analyzer. A pattern is ascertainable by the inventive technique whether the structure (pattern element) is exposed, or covered by a translucent layer.

In a preferred embodiment, the stage 31 includes known spatial encoding means to furnish spatial coordinates 70 for the position of the workpiece during the current measurements. Translational resolution of the order of 0.1 micron and rotational resolution of the order of $1\times10^{-5}$ radians is generally what is available on commercial equipment today. However, it is possible, as is known in the art, to achieve greater mechanical resolution if such is required. This additional spatial data is accessible and recordable in the memory 42. If desired, conventional spatial distributions, that is, spatial images, can be generated for any of the optical reflectance parameters. These simple 2D spatial histograms are simply pictorial representations of the physical workpiece under the constraint of the optical parameter, e.g., P or S polar light or phase difference image of the workpiece. Through the agency of the reflectance analyzer, it is the transformation of the representation of the workpiece from the spatial domain to the multidimensional reflectance (non-spatial) domain which is at the center of the invention for comparison of workpieces. For such comparisons, operations are conveniently carried out entirely in the reflectance domain. The inverse transformation to the spatial domain is also possible in the preferred embodiment, given the availability of the spatial distribution data.

Spatial encoding can be carried out with the aid of stepping motors or servo motors with an encoder and the like, together with the associated counter devices for holding the digitally encoded location information. In this way, any datum contributing to a cell of the non-spatial multi-dimensional histogram can be referenced to the spatial locus contributing that point. For example, selected cells of histogram 52 contain reflectance data that may have been acquired from a wide multiplicity of spatial locii although acquired from the scan of a single die, wafer segment or device unit. Taken as a constraining link 55 to the unsorted data, it is straightforward to associate coordinates 75 with the individual data points of the cell(s) when it is desired to obtain the spatial representation of the data from the reflectance domain, e.g., transform back to the spatial domain from histogram 52. However, this is not essential to associating features of the non-spatial histogram with the spatial images of the investigated objects. In another procedure for establishing this association, the corresponding reflectance domain histogram of a workpiece of known structural difference is compared with the respective reflectance domain histogram of a reference workpiece. The difference histogram is thus identifiable with the known physical distinction of the compared workpieces.

Although preferred, it is not essential to the invention that all optical parameters be acquired simultaneously. Optical reflectance data may be correlated in subsequent scan operations when there is accurate, and unique parameters in common between the non-concurrent measurements. Ordinarily, this is facilitated by accurate spatial encoding to yield spatial coordinates for first and subsequent scans.

In the present discussion, optical variables such as the P and S polarization components, the phase difference therebetween, and scattered light should be regarded as representative of the optical reflectance data record acquired. Functions of the reflectance parameters, appropriate to the specific acquisition instrument or the composition of the workpiece are deemed to be within the invention. Morevoer, the selection of which reflectance parameters are acquired to generate the non-spatial histograms are again determined by the nature of the investigation and the composition of the workpiece. A mass comparison screening of thousands of dice may be based upon simple 2D non-spatial histograms. It is also apparent that the information contained within a 2D histogram of optical reflectance parameters of a patterned object according to the invention, typically consumes less memory than required for storage of the spatial image of the die. A reduced memory requirement for the reflectance domain representation directly implies fewer steps necessary to complete the comparison in the reflectance domain.

Comparison of reflectance domain histograms of nominally identical patterns clearly do not require an accurate alignment of spatial or orientation of the compared objects because these quantitative values are taken in respect to an origin in reflectance space and not in respect to a spatial coordinate origin. As a practical matter, it is desired to so position the reflectance analyzer in respect to the object so that the scan limits enclose the region forming one of the pattern elements of the comparison. The pattern elements usually constitute a die and such die are positioned in known relationship on a common substrate. The relative position of a pattern element is therefore easily indexed by the precision stage 31. No mechanical alignment or orientation is required for the purpose of effecting an overlay of spatial images, nor need such steps be taken for software manipulation of images. It is apparent that comparisons between pattern elements disposed on different substrates is similarly independent of precise spatial overlay.

Conducting or dielectric features of the die may suggest different choices of reflectance parameters for comparison or general evaluation purposes. An important consideration for the formation and analysis of multidimensional histograms is the choice of data sets used. On commercially available surface reflectance analyzer currently available (HDI Instrumentation of Santa Clara, Calif.) there are four unique data channels. These are P polar reflectivity, phase contrast, enhanced phase contrast, and scattered light. If one is performing a 2D histogram base analysis there are 6 unique combinations of these channels that can be analyzed.

The choice of multiple dimensional histogram to be used for analysis will depend upon the data desired. For example if analyzing thin films for their thickness and composition, in accordance with the manufacturer's recommendations, one would use the phase contrast and P polar reflectivity channels of the SRA (see discussion in Vurens and Klein SPIE Vol 3619, 1999, page 27). However, if one is analyzing defects to determine if they are particles or dings, it is preferred to use a histogram of the scattered and phase channels of the SRA.

In general, although this invention has generally been described in connection with a surface reflectance analyzer or processing with such instrumentation, it is intended to encompass within its scope any process or equipment that takes correlated optical or equivalent electron-optical data sets that benefit from multi-dimensional histogram analysis similar to that of the SRA unit that has been discussed. Some specific examples include but are not limited to ellipsometry embodiments that measure the parameters psi, del, and reflectivity; color video imaging (which measures the parameters red, green, blue (RGB); or cyan, yellow, magenta, black (CMYK)); scatterometry (which measures scattering with different polarization, or at a different scattering angle); scanning electron microscopy (which measures back scatter, dark field, secondary electron); and, microscopy (dark field, bright field).

While this invention has been described with respect to particular embodiments, it will be apparent to those skilled in the art that various changes and modifications may be made without departing from the invention described herein.

What is claimed is:

1. The method of comparing areas of patterned surfaces intended to substantially conform to one another comprising
making a multi-dimensional reflectance histogram of a first patterned surface including systematically ordered features which exhibit substantial discontinuities or possess relatively large spatial derivatives by making at least two independent measurements with different types of detectors by scanning said first surface with an optical reflectance analyzer;
making a second multi-dimensional reflectance histogram of a, second patterned surface by making at least two independent measurements with different types of detectors by scanning said second surface with a like optical reflectance analyzer; and,
comparing said first and second histograms with each other to determine whether substantial differences exist between said histograms.

2. The method of claim 1 in which an optical reflectance analyzer employs polarized incident light.

3. The method of claim 2 in which the differences between said histograms is determined and a reverse transform to the spatial domain is performed and the actual points of differences are identified on said patterned surfaces.

4. The method of claim 3 comprising making the two measurements at the same time.

5. The method of claim 1 in which an optical reflectance analyzer employs polarization analysis of reflected light.

6. The method of claim 1 in which P polar reflectivity, phase contrast, enhanced phase contrast and scattered light data channels are available using said optical reflectance analyzers and in which at least two of these data channels are used in making histograms for comparison with each other.

7. The method of claim 1 in which the histograms are based on P polar reflectivity, and phase contrast measurements taken from the patterned surfaces being compared.

8. The method of determining conformity between die, comprising patterned surfaces on wafers, comprising:
subjecting a wafer having complex patterns of multiple and overlapping films on its surface to a first inspection of its patterned surface by using polarized light techniques;
making a multi-dimensional reflectance histogram from the data detected during inspection using two different detector systems receiving information from the same point;
generating a second multi-dimensional reflectance histogram using data obtained by subjecting another like patterned area of a surface of a wafer under inspection to a second inspection by a like analysis technique to the technique used in said first inspection; and,
comparing said histogram from said first inspection to said histogram from said second inspection to determine whether the die are the same.

9. The method of surface analysis of a patterned surface comprising generating data capable of creating at least a $2d$ histogram by polarizing the output of a laser to produce light in first and second polarization states;
directing said polarized light angularly to impinge on a first point on a first patterned workpiece including systematically ordered spatial and compositional features to be examined;
capturing the specularly reflected light from said workpiece and analyzing therefrom polar components of the reflected light;
capturing the diffuse scattered light from said workpiece and analyzing said captured scattered light;
moving the workpiece relative to the point of impingement of said light to an adjacent point from said first point on said workpiece;
employing a selected combination of at least any two of said outputs to define at least a $2d$ histogram of said first patterned workpiece; and, comparing said 2D histogram outputs from said first patterned workpiece to a like constructed 2D histogram of a like second patterned workpiece to determine whether the workpieces examined have the substantially the same patterned surface.

10. The method of claim 9 including determining the phase difference of said analyzed polar components of said reflected light.

11. An inspection tool to determine conformity of a patterned surface structure disposed on a substrate to a reference patterned surface structure comprising,
a device
to generate a reference multi-dimensional histogram from at least two optically created images of said reference surface structure, each containing different non-spatial information taken at a first location on the surface of said structure; and, to generate a second multi-dimensional histogram from at least two optically created images, each containing different non spatial information, taken at a second location, distinct from said first location, on the surface of a structure to be compared to said reference structure; said tool being capable of inspecting and comparing optically accessible interfaces below the surface; and, test equipment to compare said second histogram to said reference histogram to determine whether the histograms substantially conform with one another.

12. An inspection tool in accordance with claim 11 having a device in which the two optically created images of said reference structure are taken at the same time.

13. An inspection tool in accordance with claim 12 having a device in which the two optically created images to generate the second histogram are taken at the same time.

14. The inspection tool of claim 11 in which said light source to create the optically created images comprises polarized light.

15. Apparatus to determine conformity of a die structure disposed on a wafer to a reference structure, comprising an optical reflectance measuring device including support for a wafer and support for a control reference structure, said reflectance device for optically sampling each said structure at a corresponding plurality of locii thereon and concurrently acquiring at least two optical reflectance parameters including at least two readings of information from the same point using at least two different detection schemes characterizing each said sample, a sorting device for creating respective multi-dimensional non-spatial histograms for each said surface structure, whereby said structures are each represented by respective histograms, and a comparator for comparing corresponding said histograms.

* * * * *